United States Patent [19]
Hirao et al.

[11] Patent Number: 6,124,437
[45] Date of Patent: Sep. 26, 2000

[54] IMMUNOGLOBULIN PREPARATION AND PREPARATION PROCESS THEREOF

[75] Inventors: Yutaka Hirao; Motonori Hashimoto; Tae Kitamura; Yahiro Uemura, all of Osaka, Japan

[73] Assignee: Welfide Corporation, Osaka, Japan

[21] Appl. No.: 09/040,400

[22] Filed: Mar. 18, 1998

[30] Foreign Application Priority Data

Mar. 19, 1997 [JP] Japan ..................... 9-066441
Mar. 19, 1997 [JP] Japan ..................... 9-066448

[51] Int. Cl.[7] ................ C07K 16/00; A61K 38/21
[52] U.S. Cl. ................... 530/387.1; 530/388.25; 530/389.1; 530/390.1; 530/390.5; 530/402; 530/412; 530/414; 530/416; 530/427; 424/85.5
[58] Field of Search ............ 530/387.1, 388.25, 530/389.1, 390.1, 390.5, 402, 412, 414, 416, 427; 424/85.5

[56] References Cited

U.S. PATENT DOCUMENTS

| | | | |
|---|---|---|---|
| 4,093,606 | 6/1978 | Coval | 530/387.1 |
| 4,318,902 | 3/1982 | Stephan | 530/390.1 |
| 4,371,520 | 2/1983 | Uemura et al. | 530/387.1 |
| 4,396,608 | 8/1983 | Tenold | 530/387.1 |
| 4,499,073 | 2/1985 | Tenold | 530/387.1 |
| 4,540,573 | 9/1985 | Neurath et al. | 530/390.1 |
| 4,721,777 | 1/1988 | Uemura et al. | 530/390.1 |
| 4,762,714 | 8/1988 | Mitra et al. | 530/390.1 |
| 4,820,805 | 4/1989 | Neurath et al. | 530/410 |
| 4,835,257 | 5/1989 | Friedrich-Fietchl et al. | 530/387.1 |
| 4,841,023 | 6/1989 | Horowitz | 530/351 |
| 4,845,199 | 7/1989 | Hirao et al. | 530/387.5 |
| 4,874,708 | 10/1989 | Makula et al. | 435/272 |
| 4,876,088 | 10/1989 | Hirao et al. | 530/387.1 |
| 5,110,910 | 5/1992 | Tsav | 530/390.1 |
| 5,132,406 | 7/1992 | Uemura et al. | 530/390.1 |
| 5,177,194 | 1/1993 | Sarno et al. | 530/412 |
| 5,190,752 | 3/1993 | Möller et al. | 424/85.5 |
| 5,371,196 | 12/1994 | Yuki et al. | 530/390.1 |

FOREIGN PATENT DOCUMENTS

| | | |
|---|---|---|
| 0196761 | 10/1986 | European Pat. Off. . |
| 0702960 | 2/1995 | European Pat. Off. . |
| 0758656 | 2/1997 | European Pat. Off. . |
| 3604947 | 8/1987 | Germany . |
| 9503826 | 7/1994 | WIPO . |
| 9609839 | 9/1994 | WIPO . |
| WO9503826 | 2/1995 | WIPO . |
| WO 95/16701 | 6/1995 | WIPO . |
| WO9635710 | 11/1996 | WIPO . |

OTHER PUBLICATIONS

Hanna et al.: "Removing specific cell . . . " Biopharm, vol. 4, No. 9, 1991, pp. 33–37, XP002070853.

Saksena et al.: "Effect of solution pH and ionic strength . . . " Biotechnol. Bioeng., vol. 43, No. 10, 1994, pp. 960–968, XP002070854.

Krishnan et al.: "Ultrafiltration in pufification of . . . " Downstream Process. Biotechnol. Proc. Int. Semin: Meeting Date 1991, Tata McGraw–Hill, New Dehli, India, 1992, pp. 175–91 XP002070855.

Zborowshi et al.: "Pore size and effects in . . . " Asaio Transactions, vol. 36, No. 3, 1990, pp. M730–3, XP002070856.

*Primary Examiner*—Christopher S. F. Low
*Assistant Examiner*—Abdel A. Mohamed
*Attorney, Agent, or Firm*—Sughrue, Mion, Zinn, Macpeak & Seas, PLLC

[57] ABSTRACT

An immunoglobulin preparation comprising an immunoglobulin, wherein the preparation contains, as a contaminant, serum albumin in an amount not greater than 10 μg per 50 mg of immunoglobulin; and/or wherein the preparation is free of fine particles which can serve as a nucleus of insoluble foreign matter, and processes for preparing the immunoglobulin preparation are described.

26 Claims, No Drawings

IMMUNOGLOBULIN PREPARATION AND PREPARATION PROCESS THEREOF

BACKGROUND OF THE INVENTION

1. Field of the Invention

This invention relates to an immunoglobulin preparation, more specifically, an immunoglobulin preparation having excellent storage stability.

2. Description of the Related Art

Among γ-globulins which are plasma protein components, an immunoglobulin preparation comprising IgG has been used for preventing and treating various infectious diseases. The immunoglobulin is unstable in the form of a solution. It is known that as a result of the aggregation of immunoglobulin, in other words, as a result of the denaturation of the immunoglobulin during the fractionating operation resulting in the formation of a polymer or dimer of immunoglobulin, the immunoglobulin shows a marked increase in the complement-fixing property which is called anticomplementary action, leading to a) lowering the serum complement concentration upon intravenous administration to a human body or b) serious side effects such as anaphylactic shock. Accordingly, immunoglobulin has been formulated not as a liquid preparation but as a dry preparation, particularly, in a lyophilized form. However, the dry preparation is accompanied with the problem that it cannot be administered easily because of the necessity of dissolving it in distilled water for injection or the like upon use.

On the other hand, the liquid preparation does not require any dissolving operation in distilled water for injection or the like and can be administered easily compared with the dry preparation. As described above, however, it is accompanied with such drawbacks as inferiority in the stability of immunoglobulin. Accordingly, there has conventionally been an attempt to develop a liquid composition of immunoglobulin for intravenous injection having stability even in the form of a solution.

For example, JP-A-63-192724 (the term "JP-A" as used herein means an "unexamined published Japanese patent application" (U.S. Pat. No. 4,876,088, EP 278422)) discloses a liquid globulin composition for intravenous injection having stability even in the form of a solution, said composition having a low conductivity and pH of 5.5±0.2 and containing sorbitol as a stabilizer. In addition, JP-A-58-43914 (U.S. Pat. Nos. 4,396,608 and 4,499,073, EP 73371) discloses that in order to obtain an immunoglobulin composition which is substantially free of an aggregate of immunoglobulin and has a monomer content of immune serum globulin exceeding about 90%, a solution of the immune serum globulin is adjusted to have an ionic strength less than about 0.001 and a pH of 3.5 to 5.0.

JP-A-63-8340 (U.S. Pat. Nos. 4,762,714 and 4,948,877, EP 240856) discloses a process for preparing immune serum globulin substantially free of an acquired virus, which comprises obtaining immune serum globulin from the human plasma source by the cold ethanol fractionating method at a pH of about 5.4 or lower and storing the immune serum globulin at a pH of about 4.25 or lower for at least about three days or storing it at a pH of about 6.8 or lower and a temperature of at least 45° C. so as not to contain an infectious retrovirus substantially. However, the above-described invention aims at the inactivation of a retrovirus. It has not been reported that the immunoglobulin preparation thus obtained shows an improvement in the aggregation-wise problem of immunoglobulin.

JP-A-7-238036 (EP 702960) discloses that for the improvement of stability, the aggregation of immunoglobulin, in other words, an increase of not only a polymer of immunoglobulin but also a dimer of immunoglobulin is suppressed by acid treatment or storage at room temperature.

WO 95-3826 discloses the immunoglobulin preparation comprising 0.1 g/L or less of non-ionic surfactant as stabilizer for maintaining solution state, and being substantially free of albumin.

SUMMARY OF THE INVENTION

As described above, immunoglobulin is essentially an unstable protein so that the stability thereof upon preparation of a liquid composition is one of the great concerns.

An object of the present invention is to overcome the above-described problem and hence to provide an immunoglobulin preparation having good storage stability even in the form of a solution.

With the foregoing in view, the present inventors have proceeded with an extensive investigation. As a result, they have been found that storage stability of immunoglobulin can be improved by reducing an amount of serum albumin existing as a contaminant in an immunoglobulin fraction to a trace amount, leading to the completion of the present invention.

The present inventors built up a hypothesis that fine particles existing in an immunoglobulin preparation would be a nucleus for forming insoluble foreign matter. It has been found based on that hypothesis that the storage stability of the immunoglobulin preparation can be improved by removing fine particles which may be a nucleus for forming the insoluble foreign matter, leading to the completion of the present invention.

This and other objects of the present invention have been accomplished by:

1) an immunoglobulin preparation (composition) comprising an immunoglobulin, wherein said preparation contains, as a contaminant, serum albumin in an amount not greater than 10 μg per 50 mg of immunoglobulin;

2) an immunoglobulin preparation (composition) comprising an immunoglobulin, wherein said preparation is free of fine particles which can serve as a nucleus of insoluble foreign matter; and 3) a process for preparing the above immunoglobulin preparation 1) or 2), which comprises at least one step of:

treating an aqueous immunoglobulin-containing solution with an anion exchanger;

treating an aqueous immunoglobulin-containing solution with colloidal silica; and filtrating an aqueous immunoglobulin-containing solution through a porous membrane having an average pore size of 1 to 100 nm.

DETAILED DESCRIPTION OF THE INVENTION

The present invention will hereinafter be described more specifically. No particular limitation is imposed on the mode of immunoglobulin used for the immunoglobulin preparation of the- present invention; however, any mode of immunoglobulin available in the art can be used. Examples include immunoglobulin prepared using, as a starting material, a fraction containing immunoglobulin, more specifically, fractions II+III, fraction II available by Cohn's ethanol fractionation, and paste of a similar fraction thereto containing immunoglobulin. A method of suspending such a fraction in an aqueous solvent to extract immunoglobulin can be used as a preparation process of immunoglobulin. At this time, an aqueous medium at least twice the volume, preferably, at least 5 times the volume of said fraction is used. Preferred examples of the aqueous medium usable here include water and an aqueous solution containing sodium chloride, hydrochloric acid, acetic acid or phosphoric acid, or a salt thereof. In addition, preferably, the pH ranges from 4 to 7, and the ionic strength ranges from 0.001 to 0.1 M.

Examples of immunoglobulin include a chemical-modification free and complete-molecule immunoglobulin (for example, an immunoglobulin treated with polyethylene glycol, a pH about 4, or an ion exchange resin); a chemically modified immunoglobulin (for example, an alkylated or sulfonated immunoglobulin); and an enzyme-treated immunoglobulin (for example, an immunoglobulin treated with an enzyme such as plasmin, pepsin or trypsin). Among these, a chemical-modification free and complete-molecule immunoglobulin is used preferably.

The term "chemical-modification free and complete-molecule immunoglobulin" as used herein means an immunoglobulin having the following various properties:

1) immunoglobulin which is intact (natural) and not subjected to any artificial modification or change and therefore does not contain fragments of immunoglobulin such as Fab, F(ab')$_2$ and Fc;

2) immunoglobulin free from causing a lowering in the antibody titer and also absent diminishment in the antibody spectrum; and 3) immunoglobulin having an anticomplementary action (complement fixing property) sufficiently lower than 20 units (CH50 value) which is a value regarded safe in the Japanese Biological Preparation Standards.

As such a chemical-modification free and complete-molecule immunoglobulin, that obtained by any method can be used insofar as it is intact (natural) and has a low anticomplementary activity.

The chemical-modification free and complete-molecule immunoglobulin may be prepared in any manner. Examples include ethanol fractionation, polyethylene glycol fractionation (JP-A-53-47515 (U.S. Pat. Nos. 4,093,606 and 4,124,576)), fractionation by polyethylene glycol and hydroxyethyl starch used in combination (JP-A-51-91321), acid treatment (JP-A-57-32228 (U.S. Pat. No. 4,371,520, EP 78331)), bentonite treatment (JP-A-57-77623) anion exchanger treatment [JP-W-59-501546 (the term "JP-W" as used herein means a "published unexamined international application"), JP-A-60-42336], a combination of heating treatment and polyethylene glycol fractionation (JP-A-63-183539 (U.S. Pat. No. 5,132,406, EP 246579)), and formulation into a liquid preparation (JP-A-58-43914 (U.S. Pat. Nos. 4,396,608 and 4,499,073, EP 73371), JP-A-63-197274 (U.S. Pat. No. 4,876,088, EP 278422)).

Preferably, the immunoglobulin obtained by one of the above methods is subjected to heating treatment. Examples of the method for heating it in the form of a liquid include a method of using a highly-concentrated sugar or sugar alcohol as a stabilizer (JP-A-61-191622 (EP 196761)) and a method of carrying out heating treatment at a low ionic strength and at an acid pH by using a highly-concentrated sorbitol as a stabilizer (JP-A-63-146832 (U.S. Pat. No. 4,845,199, EP 253313)). Examples of the method for heating it in the dry form, on the other hand, include a method of using glycine, polyethylene glycol, sodium chloride, mannitol or the like as a stabilizer (JP-A-61-78730 (U.S. Pat. No. 4,721,777, EP 177836)) and a method of using a disaccharide or sugar alcohol as a stabilizer (JP-A-62-228024, JP-A-63-283933).

Also, the immunoglobulin may be subjected to virus-inactivating treatment other than heating treatment. Examples thereof include trialkyl phosphate and/or detergent treatment (U.S. Pat. No. 4,540,573, EP 131740), membrane filtration (WO 96-9839).

No particular limitation is imposed on the source of the immunoglobulin used in the present invention. Specific examples include human, mouse and rat. Among these, human is preferred. Specific example of the immunoglobulin include a human immunoglobulin treated with polyethylene glycol.

The immunoglobulin preparation according to the present invention includes a preparation from which serum albumin as contaminant have been removed to some extent. Examples of methods for removing serum albumin include a contact treating method with an anion exchanger and a contact treating method with colloidal silica which will be described below.

A) Treatment with an Anion Exchanger

This is a method of recovering a non-adsorbed fraction by the contact treatment with an anion exchanger.

i) Preparation of an Anion Exchanger

An anion exchanger is an insoluble carrier having an anion exchange group bonded thereto. Examples of the anion exchange group usable here include a diethylaminoethyl (DEAE) group and a quaternary aminoethyl (QAE) group. Examples of the insoluble carrier include agarose, cellulose, dextran and polyacrylamide. They can be bonded in a manner known in the art.

ii) Treating Method

An immunoglobulin fraction is dissolved in an appropriate aqueous solvent. The aqueous medium is preferred to have a pH of 4 to 7 (more preferably pH 5 to 6), and a low ionic strength (more preferably 0.0001 to 0.1 M). Examples of such an aqueous medium include an aqueous solution of sodium chloride, distilled water for injection and an acetate buffer. The immunoglobulin solution thus prepared is preferred to have a protein concentration of 1 to 15 w/v % (more preferably 3 to 10 w/v %) and a pH of 4 to 7 (more preferably 5 to 6).

The immunoglobulin solution thus prepared can then be subjected to contact treatment with an anion exchanger equilibrated with the above-described aqueous medium. Examples of this treatment include a batch method or a column method. In the batch method, for example, about 10 to 100 ml of an immunoglobulin solution are mixed with about 1 ml of an anion exchanger, the resulting mixture is stirred at 0 to 4° C. for about 30 minutes to 2 hours and then the reaction mixture is centrifuged at 6000 to 8000 rpm for 10 to 30 minutes to recover a supernatant. In the column method, on the other hand, for example, about 10 to 100 ml of an immunoglobulin solution is brought into contact with about 1 ml of an anion exchanger to recover a non-adsorbed fraction.

B) Treatment with Colloidal Silica

This is a method of recovering a non-adsorbed fraction by contact treatment with colloidal silica.

i) Adsorbent

Examples of the colloidal silica used as the adsorbent include silica gel, light silicic anhydride, diatomaceous earth, acid clay, bentonite, kaolin and magnesium silicate aluminate. Preferably, light silicic anhydride ("Aerosil", trade name; product of Nippon Aerosil Co., Ltd. and "Delipid", trade name; product of Zeta Inc.) are employed.

ii) Treating Conditions

The purified immunoglobulin is dissolved in an appropriate aqueous solvent. The aqueous medium is preferred to have a pH of 4 to 7 (more preferably 5 to 6) and a low ionic strength (more preferably 0.0001 to 0.1 M). Examples of the aqueous medium include those exemplified above in the treatment with the anion exchanger. The immunoglobulin solution thus prepared is preferred to have a protein concentration of 1 to 15 w/v % (more preferably 3 to 10 w/v %) and a pH of 4 to 7 (more preferably pH 5 to 6).

The immunoglobulin solution thus prepared may contain a pharmaceutically acceptable additive (for example, carrier, excipient, diluent), stabilizer and/or a pharmaceutically necessary component which is used ordinarily for pharmaceuticals within an extent not impairing the object of the present invention.

Examples of the stabilizer include monosaccharides (for example, glucose), disaccharides (for example, saccharose, maltose), sugar alcohols (for example, mannitol, sorbitol), neutral salts (for example, sodium chloride), amino acids (for example, glycine), and nonionic surfactant (for example, polyethylene glycol, polyoxyethylene-polyoxypropylene copolymer ("Pluronic", trade name), polyoxyethylene sorbitan fatty acid ester ("Tween", trade name)). The stabilizer is preferably added in an amount of about 1 to 10 w/v %.

Then, the immunoglobulin solution is subjected to contact treatment with the above-described adsorbent. As the contact treatment conditions to be employed, the adsorbent is used in an amount of 1 to 30 g/liter when the concentration of immunoglobulin is 1 to 100 g/liter (more preferably 10 to 100 g/liter). This treatment can be carried out, for example, by either a batch method or a column method. Among these, a batch method is preferred. In the batch method, mixing and stirring are conducted under conditions, for example, at 5 to 25° C. for about 5 minutes to 1 hour. Then, the supernatant (non-adsorbed fraction) can be recovered by, for example, filtration or centrifugation.

The immunoglobulin preparation from which serum albumin has been removed contains a contaminant of serum albumin in an amount not greater than 10 $\mu$g, preferably not greater than 5 $\mu$g, per 50 mg of immunoglobulin. Specifically, when the immunoglobulin preparation is in the form of a solution containing 5 w/v % of immunoglobulin, it contains a contaminant of serum albumin in an amount not greater than 10 $\mu$g/ml, preferably not greater than 5 $\mu$g/ml. The immunoglobulin preparation having such properties exhibits more excellent storage stability than the conventional one. For example, even after storage at 25° C. for at least 30 days under shaking, or even at 37° C. for at least 39 days, the immunoglobulin preparation in the form of a solution is free of insoluble foreign matter. That is, insoluble foreign matter is not visually observed. As the assay of serum albumin in the immunoglobulin preparation, methods known in the art can be employed. Examples include, ELISA method, Mancini's method and nephelometry.

C) Treatment with a Porous Membrane

The immunoglobulin preparation according to the present invention includes a preparation from which fine particles which can serve as a nucleus for the formation of insoluble foreign matter have been removed. Examples of removal methods include filtration methods through a porous membrane (for example, in the form of a hollow yarn or a sheet).

No particular limitation is imposed on the material of the porous membrane usable in the present invention. Preferred is regenerated cellulose. Examples of the form of the membrane include a hollow yarn and a sheet, with hollow yarn being preferred. For example, the porous hollow yarn made of regenerated cellulose is prepared preferably from an ammonium cupricellulose solution by the micro phase separation method [American Chemical Society, 9:197-228 (1985)].

The average pore size of the porous membrane is 1 to 100 nm, preferably 10 to 75 nm, more preferably 10 to 50 nm, and most preferably 35±2 nm. Its thickness is preferably 35±3.5 $\mu$m. The membrane has preferably a multilayer structure. When the porous membrane is in the form of a hollow yarn, its internal diameter is preferably 330±30 $\mu$m.

When the porous membrane is in the form of a hollow yarn, it is preferably used in the mode of a module. The module is composed of a porous hollow yarn membrane having preferably a membrane area of 0.001 to 1.0 $m^2$, a container to be filled with the membrane and an adhesive to integrate them.

Filtration treatment through the porous membrane is carried out, for example, as follows:

An immunoglobulin fraction is first dissolved in an appropriate aqueous solvent. The aqueous medium is preferred to have a pH of 4 to 7 (more preferably pH 5 to 6) and a low ionic strength (more preferably 0.0001 to 0.1 M). Examples of the aqueous medium include an aqueous solution of sodium chloride, distilled water for injection and an acetate buffer. The immunoglobulin solution thus prepared is preferred to have a protein concentration of 1 to 15 w/v % (more preferably 3 to 10 w/v %) and a pH of 4 to 7 (more preferably 5 to 6).

The immunoglobulin solution thus prepared may contain a pharmaceutically acceptable additive (for example, carrier, excipient, diluent), stabilizer and/or a pharmaceutically necessary component which is used for pharmaceuticals within an extent not impairing the object of the present invention.

Examples of the stabilizer include monosaccharides (for example, glucose), disaccharides (for example, saccharose, maltose), sugar alcohols (for example, mannitol, sorbitol), neutral salts (for example, sodium chloride), amino acids (for example, glycine) and nonionic surfactants (for example, polyethylene glycol, polyoxyethylene-polyoxypropylene copolymer ("Pluronic", trade name), polyoxyethylene sorbitan fatty acid ester ("Tween", trade name)). The stabilizer is preferably added in an amount of about 1 to 10 w/v %.

The above-described immunoglobulin-containing solution is filtered through a porous membrane. The filtration pressure or force at this time is 0.1 to 1 $kgf/cm^2$, preferably 0.1 to 0.5 $kgf/cm^2$, more preferably 0.1 to 0.3 $kgf/cm^2$. The treating temperature is preferably 4 to 50° C.

Examples of the mode of the filtration treatment include the cross flow filtration method (circulation type) in which filtration is effected while a straining rate is given to a liquid and the dead end filtration method (non circulation type) in which filtration is carried out without giving a straining rate. The cross flow filtration method by pressed air is preferably adopted.

The filtration treatment can be carried out plural times. Prior to the above filtration treatment, the immunoglobulin-containing solution may be subjected to another filtration treatment.

The immunoglobulin preparation thus prepared is a preparation from which insoluble fine particles having an average particle size not smaller than 100 nm, preferably not smaller than 75 nm, more preferably not smaller than 35 nm and/or soluble fine particles having a molecular weight larger than that of the immunoglobulin (about 150000 Daltows), both of which may become a nucleus for forming insoluble foreign matter, have been removed, so that even if the immunoglobulin preparation in the form a solution is stored at 25° C. for at least 30 days under shaking or at 37° C. for at least 39 days, it does not cause aggregation of immunoglobulin, that is, generation of insoluble foreign matter, and exhibits good storage stability. That is, insoluble foreign matter is not visually observed.

In the present invention, the above-described contact treatment with an anion exchanger or colloidal silica and filtration treatment through a porous membrane may be used in any combination thereof or alone, and the order of the treatments is not limited. However, preferably, the treatment with an anion exchanger, the treatment with colloidal silica and the treatment with a porous membrane are used in this order.

D) Final Preparation (Particularly Liquid Preparation)

i) Preparation of Liquid Preparation

By using the above-described method for preparing an immunoglobulin preparation for intravenous injection according to the present invention, an immunoglobulin preparation for intravenous injection can be obtained. In a preferred embodiment, a chemical-modification free and complete-molecular immunoglobulin liquid composition (preparation) which can be administered intravenously can be obtained by adjusting an aqueous solution of a chemical-modification free and complete-molecular immunoglobulin to have a concentration of 1 to 10 w/v % (more preferably 3 to 7 w/v %) by the conventional method, adjusting the resulting solution to contain a stabilizer, for example, sorbitol in an amount of 1 to 20 w/v % (more preferably 2 to 10 w/v %), to pH 5 to 6 (more preferably pH 5.5±0.2) and to have a low conductivity (more preferably a conductivity not higher than 1 mmho, more preferably not higher than 0.6 mmho, each calculated in terms of 8° C.) by known methods and then subjecting the resulting solution to sterilizing filtration, pouring in portions and the like based on the ordinary formulating technique.

From the preparation thus formed, an immunoglobulin liquid preparation for intravenous injection which contains chemical-modification free and complete-molecular immunoglobulin, has a pH of 5 to 6 (more preferably about 5.5±0.2) and a conductivity not greater than 1 mmho (more preferably not greater than 0.6 mmho, each calculated in terms of 8° C.), that can be stored at room temperature, has an anticomplementary titer not greater than 20 units and has a content of the dimer of immunoglobulin not greater than 7% can be produced.

When a safety range of the content of the immunoglobulin dimer is taken into consideration with regard to an immunoglobulin-containing preparation for intravenous injection which comprises chemical-modification free and complete-molecular immunoglobulin, the content of the immunoglobulin dimer is set at 7% or below, preferably 6% or below, and most preferably 4% or below.

The preparation according to the present invention has immunoglobulin not substantially inactivated, contains neither an IgG polymer nor contaminant, has good solubility and has sufficiently low anticomplementary action and is a safe preparation which can pass the biological preparation standards when a virus is inactivated, for example, by heating treatment.

The immunoglobulin preparation according to the present invention can be used as is or can be diluted with an appropriate solvent (for example, distilled water for injection, physiological saline, glucose solution) when it is a liquid preparation. When it is a dry preparation, on the other hand, the above-described immunoglobulin solution is lyophilized. It is dissolved in an appropriate solvent (for example, distilled water for injection) upon use.

The administration route of the immunoglobulin preparation according to the present invention is generally by injection, with intravenous administration being preferred. The immunoglobulin preparation of the present invention is preferably administered intravenously in an amount of 50 to 1000 mg/day per 1 kg of body weight as immunoglobulin for one day or for several possibly consecutive days. The dose may be increased or decreased based on the symptom, sex, body weight or the like of a patient.

The immunoglobulin preparation according to the present invention is a preparation from which fine particles, which can be a nucleus for forming insoluble foreign matter, have been removed so that it has improved storage stability.

In addition, owing to a small amount of serum albumin as a contaminant, the immunoglobulin preparation according to the present invention does not form insoluble foreign matter even in the form of a solution, compared with the conventional one and therefore has improved storage stability.

The present invention will hereinafter be described more specifically by examples and tests. It should however be borne in mind that the present invention is not limited to or by them.

EXAMPLE 1

A paste (1 kg) of Fractions II+III obtained by the Cohn's cold alcohol fractionation method was dissolved in 10 liters of 0.6 w/v % sodium chloride. The resulting solution was adjusted to pH 3.8 with 1 N hydrochloric acid and stirred at 4° C. for 60 minutes, followed by acid treatment. While 500 g of polyethylene glycol having an average molecular weight of 4000 were added thereto and dissolved, 1 N sodium hydroxide was further added thereto to gradually increase its pH to 5.0. Immediately thereafter, the precipitate was removed by centrifugation to obtain a clear supernatant. Polyethylene glycol (700 g) having an average molecular weight of 4000 was added to the supernatant. The resulting mixture was adjusted to pH 8.0 with 1 N sodium hydroxide under stirring gently. The immunoglobulin thus precipitated was recovered by centrifugation.

The immunoglobulin thus recovered was dissolved in a) physiological saline, or b) 0.02 M acetate buffer containing 0.6 w/v % sodium chloride and 2 w/v % mannitol. A 5 w/v % solution of immunoglobulin was allowed to pass through a filter carrying anhydrous silica ("Zeta Delipid", trade name; product of Quno Corp.) to recover a non-adsorbed fraction. The non-adsorbed fraction was subjected to sterilizing filtration and lyophilization to obtain an immunoglobulin preparation for intravenous administration suited for clinical use.

As a result of the assay by the Mancini's method, the albumin contained in the 5 w/v % solution of the immunoglobulin preparation thus obtained was found to be 10 $\mu$g/ml or less.

EXAMPLE 2

To 1 kg of Cohn's fractions II+III obtained from the human plasma by the cold ethanol method, 10 liters of water were added, followed by extraction of IgG. After 50 g of sorbitol were added per 100 ml of the resulting supernatant and its pH was adjusted to 5.5, the resulting mixture was heated to 60° C. for 10 hours. Then, the reaction mixture was adjusted to pH 5.5 and diluted three-fold with cold water for injection. To the diluted liquid, polyethylene glycol (average molecular weight: 4000) was added to give a final concentration of 8 w/v %. The resulting mixture was centrifuged at 2° C. to obtain a supernatant. To the supernatant, 1 N sodium hydroxide was added to adjust its pH to 8.8, and then polyethylene glycol (average molecular weight: 4000) was added thereto to give a final concentration of 12 w/v %. The resulting mixture was centrifuged at 2° C. to obtain an IgG fraction precipitated. The IgG fraction thus obtained was dissolved in water for injection. To the resulting solution, DEAE-Sephadex equilibrated with water for injection was added (about 2 ml per 50 ml of the solution). Under a temperature of 0 to 4° C., the resulting mixture was subjected to contact treatment for about one hour. After the treatment, the DEAE-Sephadex was removed by filtration to recover a filtrate (IgG solution).

The IgG solution thus recovered was diluted into a 5 w/v % solution with water for injection, and its pH was adjusted to about 5.5 with sodium acetate. Sorbitol was then added thereto to give a final concentration of 5%. The aqueous solution thus obtained (conductivity: about 1 mmho) was allowed to pass through a filter carrying anhydrous silica similar to Example 1 to recover a non-adsorbed fraction. The non-adsorbed fraction was further sterilized by filtration to obtain an immunoglobulin preparation for intravenous administration.

The amount of albumin mixed in the resulting 5 w/v % IgG solution was found to be 5 $\mu$g/ml as a result of the assay by the Mancini's method.

TEST EXAMPLE 1

The immunoglobulin preparation (5 w/v % solution) of the present invention which had been treated with colloidal silica and that without the treatment were compared in the contaminant amount of serum albumin in the immunoglobulin solution and the formation degree of insoluble foreign matter after storage at 37° C. for 39 days. The treatment with colloidal silica was carried out in accordance with the method as described in above Examples. For the assay of serum albumin, the Mancini's method was employed and insoluble foreign matter was observed visually. The results are shown in Table 1.

TABLE 1

|  | Treated with colloidal silica | Not treated with colloidal silica |
|---|---|---|
| Content of serum albumin ($\mu$g/ml) | 3 | 47 |
| Insoluble foreign matter |  |  |
| Just before storage | – | – |
| Day 39 after storage | – | ++ |

–: No insoluble foreign matter was observed.
+: Some insoluble foreign matter was observed.
++: Insoluble foreign matter was observed definitely.

The above results show that the immunoglobulin preparation treated with colloidal silica contains serum albumin in a markedly small amount and no insoluble foreign matter is observed even after storage at 37° C. for 39 days.

EXAMPLE 3

The paste (1 kg) of Fractions II+III obtained by the Cohn's cold alcohol fractionating method was dissolved in 10 liters of 0.6 w/v % sodium chloride, and its pH was adjusted to 3.8 with 1 N hydrochloric acid. The resulting solution was subjected to acid treatment at 4° C. for 60 minutes. While 500 g of polyethylene glycol having an average molecular weight of 4000 were added thereto and dissolved, 1 N sodium hydroxide was added thereto to gradually increase its pH to 5.0. Immediately thereafter the precipitate was removed by centrifugation to obtain a clear supernatant. To the supernatant, 700 g of polyethylene glycol having an average molecular weight of 4000 were added. The resulting mixture was adjusted to pH 8.0 with 1 N sodium hydroxide under stirring gently. The immunoglobulin thus precipitated was centrifuged and the immunoglobulin thus recovered was dissolved in a) physiological saline, or b) 0.02 M acetate buffer containing 0.6 w/v % sodium chloride and 2 w/v % mannitol.

Used as a porous membrane was a BBM module ("Planova 35", trade name) of a porous hollow yarn [Bemberg Microporous Membrane, which will hereinafter be abbreviated as "BMM"] produced by Asahi Chemical Industries, Co., Ltd. The porous hollow yarn used in the module has a multilayer structure of at least 150 layers and it has a pore size of 35±2 nm, a membrane area of 0.001 to 1.0 m$^2$, an internal diameter of a hollow yarn of 330±30 $\mu$m and a membrane thickness of 35±3.5 $\mu$m and is made of regenerated cellulose obtained by the cuprammonium process. The BMM module is integrated in a plastic container made of polycarbonate which can be sterilized with a high-pressure steam together with a polyurethane adhesive. Distilled water for injection fills the module. The safety of various materials constituting "Planova" has already been confirmed by the method established by the Japanese Pharmacopoeia (according to the explanatory note of BMM) hereby incorporated by reference.

The 5 w/v % immunoglobulin-containing solution was adjusted to have a pH of 6.4 to 7.2. After sterilizing filtration (pore size: 0.2 $\mu$m, filtration through a membrane filter), the resulting solution was subjected to membrane filtration treatment (dead end filtration method using air pressure) at 5° C. and a filtration pressure of 0.2 kgf/cm$^2$ for 1 to 5 hours. After cooling, sterilizing treatment was carried out again, followed by pouring in portions and lyophilization to obtain a human immunoglobulin preparation suitable for intravenous injection was prepared.

EXAMPLE 4

To 1 kg of Cohn's Fractions II+III obtained from the human plasma by the cold ethanol method, 10 liters of water were added. After 50 g of sorbitol were added per 100 ml of the resulting solution, its pH was adjusted to 5.5, and the resulting mixture was heated at 60° C. for 10 hours. Then, the reaction mixture was adjusted to pH 5.5 and diluted three-fold with cold water for injection. To the diluted liquid, polyethylene glycol (average molecular weight: 4000) was added to give a final concentration of 6 w/v %. The resulting mixture was centrifuged at 2° C. to obtain a supernatant was obtained. To the supernatant, 1 N sodium hydroxide was added to adjust its pH to 8.8, and the addition of polyethylene glycol (average molecular weight: 4000) was added thereto to give a final concentration of 12 w/v %. The resulting mixture was centrifuged at 2° C. to obtain the IgG fraction precipitated. The IgG fraction thus precipitated was dissolved in water for injection. To the resulting solution, DEAE-Sephadex equilibrated with water was added (about 2 ml per 50 ml of the solution). Under a temperature of 0 to 4° C., the resulting mixture was subjected to contact treatment for about one hour, the DEAE-Sephadex was removed by filtration to recover a filtrate (IgG solution).

The IgG solution thus recovered was diluted into a 5 w/v % solution with water for injection, and its pH was adjusted to about 5.5 with sodium acetate. Sorbitol was then added thereto to give a final concentration of 5%. The aqueous solution thus obtained was subjected to BMM treatment in the same manner as in Example 3. The aqueous solution (conductivity: about 1 mmho) was subjected to sterilizing filtration to obtain a liquid immunoglobulin preparation suitable for intravenous administration.

TEST EXAMPLE 2

A stability test against shaking at 25° C. was made to compare the polyethylene glycol-treated, chemical-modification free and complete-molecular immunoglobulin for the intravenous administration subjected to BMM treatment and that without BMM treatment. The pH during storage was set at 5.5. The evaluation was made by visually observing the formation degree of insoluble foreign matter. The results are shown in Table 2.

TABLE 2

| Time (day) | Treated with BMM | Not treated with BMM |
| --- | --- | --- |
| 0 | − | − |
| 15 | − | ++ |
| 30 | − | ++ |

−: No insoluble foreign matter is observed.
+/−: There are some cases where insoluble foreign matter is observed.
+: Some insoluble foreign matter is observed.
++: Insoluble foreign matter is observed definitely.

The above results show that the immunoglobulin preparation treated with BMM hardly forms insoluble foreign matter even after 30 days at 25° C., while insoluble foreign matters were observed definitely from the immunoglobulin preparation without BMM treatment after storage for 15 days at 25° C.

EXAMPLE 5

The IgG solution obtained in Example 2 was diluted into a 5 w/v % IgG solution with water for injection, and its pH was adjusted to about 5.5 with sodium acetate. Sorbitol was added thereto to give a final concentration of 5%. Then, the resulting mixture was treated with an anhydrous silica carrier in the same manner as in Example 2, and a non-adsorbed fraction was recovered. Then, in the same manner as in Example 4, the non-adsorbed fraction was treated with BMM to recover a non-adsorbed fraction. The resulting aqueous solution (conductivity: about 1 mmho) was subjected to sterilizing filtration to obtain an immunoglobulin liquid preparation for intravenous injection.

While the invention has been described in detail and with reference to specific embodiments thereof, it will be apparent to one skilled in the art that various changes and modifications can be made therein without departing from the spirit and scope thereof.

What is claimed is:

1. A process for preparing an immunoglobulin preparation comprising:
   treating an aqueous immunoglobulin-containing solution with colloidal silica; or
   filtrating an aqueous immunoglobulin-containing solution through a porous membrane having an average pore size of 1 to 100 nm wherein said immunoglobulin preparation remains free of insoluble material after storage at 25° C. for at least 30 days or storage at 37° C. for at least 39 days.

2. The process according to claim 1, wherein said aqueous immunoglobulin-containing solution is treated with an anion exchanger, treated with colloidal silica; and filtrated through a porous membrane having an average pore size of 1 to 100 nm, in this order.

3. The process according to claim 1, wherein said immunoglobulin-containing solution is further subjected to virus inactivating treatment.

4. The process according to claim 1, wherein said aqueous immunoglobulin-containing solution is further subjected to polyethylene glycol precipitation.

5. The process according to claim 1, which comprises:
   virus inactivating said immunoglobulin-containing solution;
   subjecting said immunoglobulin-containing solution to polyethylene glycol precipitation;
   treating said immunoglobulin-containing solution with the anion exchanger; and then treating said immunoglobulin-containing solution with colloidal silica or filtrating through the porous membrane having the average pore size of 1 to 100 nm.

6. The process according to claim 1, wherein said immunoglobulin is a chemical-modification free and complete-molecule IgG immunoglobulin.

7. The process according to claim 1, wherein fine particles are removed; said fine particles are soluble; and said fine particles have molecular weights larger than that of immunoglobulin of about 150000 Daltows.

8. The process according to claim 1, wherein said aqueous immunoglobulin-containing solution is treated with an anion exchanger in an aqueous medium at pH 4 to 7 and an ionic strength of 0.0001 to 0.1 M to recover a non-adsorbed fraction.

9. An immunoglobulin preparation obtained by the process according to claim 8.

10. The process according to claim 1, wherein said aqueous immunoglobulin-containing solution is treated with colloidal silica in an aqueous medium at pH 4 to 7 and an ionic strength of 0.0001 to 0.1 M to recover a non-adsorbed fraction.

11. An immunoglobulin preparation obtained by the process according to claim 10.

12. The process according to claim 1, wherein said aqueous immunoglobulin-containing solution is filtered through a porous membrane having an average pore size of 1 to 100 nm at pH 4 to 7 in an aqueous medium having ionic strength of 0.0001 to 0.1 M to recover a non-adsorbed fraction.

13. An immunoglobulin preparation obtained by the process according to claim 12.

14. An immunoglobulin preparation obtained by the process according to claim 1.

15. The immunoglobulin according to claim 14
   wherein said preparation contains, as a contaminant, serum albumin in an amount not greater than 10 µg per 50 mg of immunoglobulin; and
   wherein said preparation is free of fine particles which can serve as a nucleus of insoluble foreign matter.

16. The immunoglobulin according to claim 14, wherein said preparation is free of insoluble foreign matter after storage at 37° C. for at least 39 days in the form of a solution.

17. The immunoglobulin according to claim 14, wherein said preparation is free of insoluble foreign matter after storage at 25° C. for at least 30 days under shaking in the form of a solution.

18. The immunoglobulin according to claim 14, wherein said preparation has a pH of 5 to 6, a conductivity not higher than 1 mmho (calculated in terms of 8° C.), an anticomplementary value not greater than 20 units, and an IgG dimer content not higher than 7%.

19. The immunoglobulin according to claim 14, wherein said preparation is subjected to virus inactivating treatment.

20. The immunoglobulin according to claim 14, wherein said immunoglobulin is a chemical-modification free and complete-molecular immunoglobulin.

21. The immunoglobulin according to claim 14, wherein said fine particles have been removed from said preparation and said fine particles have an average particle size not smaller than 100 nm.

22. The immunoglobulin preparation according to claim 14, wherein said fine particles had been removed from said preparation and said fine particles have an average particle size not smaller than 35 nm.

23. A process for removing serum albumin from an immunoglobulin preparation, comprising:
   a) treating an aqueous immunoglobulin containing solution with an anion exchanger; and then
   b) treating an aqueous immunoglobulin-containing solution obtained in the step a) with colloidal silica wherein said immunoglobulin preparation remains free of insoluble material after storage at 25° C. for at least 30 days or storage at 37° C. for at least 39 days.

24. An immunoglobulin preparation obtained by the process according to claim 23.

25. A process for removing fine particles which can serve as a nucleus of insoluble foreign matter from an immunoglobulin preparation, comprising filtrating an aqueous immunoglobulin-containing solution through a porous membrane having an average pore size of 1 to 100 nm wherein said immunoglobulin preparation remains free of insoluble material after storage at 25° C. for at least 30 days or storage at 37° C. for at least 39 days.

26. An immunoglobulin preparation obtained by the process according to claim 25.

* * * * *